United States Patent [19]

Kollonitsch et al.

[11] 4,215,221

[45] Jul. 29, 1980

[54] FLUORINATION PROCESS

[75] Inventors: Janos Kollonitsch, Westfield; Stephen Marburg, Metuchen, both of N.J.

[73] Assignee: Merck & Co., Inc., Rahway, N.J.

[21] Appl. No.: 939,032

[22] Filed: Sep. 1, 1978

Related U.S. Application Data

[63] Continuation-in-part of Ser. No. 802,389, Jun. 1, 1977, abandoned.

[51] Int. Cl.$^2$ ................. C07D 233/64; C07D 209/20; C07C 101/72; C07C 101/77
[52] U.S. Cl. .............................. 548/344; 260/326.14 T; 562/445; 562/446; 562/449
[58] Field of Search ............... 548/344; 260/326.14 T, 260/694; 562/445, 449, 446

[56] References Cited

U.S. PATENT DOCUMENTS

| | | | |
|---|---|---|---|
| 3,413,326 | 11/1968 | Schmid | 548/344 |
| 4,004,996 | 1/1977 | Kollonitsch | 204/158 HA |

OTHER PUBLICATIONS

Kollonitsch et al. J. Org. Chem. 1975, vol. 40, pp. 3808–3809.
Hasek et al. J. Amer. Chem. Soc. 1960, vol. 82, pp. 543–551.

*Primary Examiner*—Natalie Trousof
*Attorney, Agent, or Firm*—Daniel T. Szura; Harry E. Westlake, Jr.

[57] ABSTRACT

A process for preparing α-fluoromethyl amino acids from corresponding α-hydroxymethyl amino acids is disclosed. The process utilizes $SF_4$ and $BF_3$ or $AlCl_3$ in HF to effect the fluorination.

6 Claims, No Drawings

FLUORINATION PROCESS

CROSS REFERENCE TO RELATED APPLICATIONS

This application is a continuation in part of U.S. application Ser. No. 802,389 filed June 1, 1977, now abandoned.

BACKGROUND OF THE INVENTION

The present invention is concerned with an improved process for preparing α-fluoromethylamino acids.

A process for preparing fluoromethylamino acids from the corresponding hydroxymethylamino acids using $SF_4$ in liquid HF to effect the fluorination is known (Kollonitsch et al., J. Org. Chem. 40 3808-9-1975). The process is referred to as fluorodehydroxylation.

It has now been discovered that the fluorodehydroxylation of certain aryl substituted α-hydroxymethyl-α-amino acids is substantially improved by utilizaing $BF_3$ or $AlCl_3$ as a co-reactant with $SF_4$.

SUMMARY OF THE INVENTION

Process for preparing α-fluoromethyl aryl-substituted-α-amino acids comprising the reaction of an α-hydroxymethyl aryl substituted α-amino acid with (a) $SF_4$ and (b) $BF_3$ or $AlCl_3$, in liquid HF at temperatures ranging from about −80° C. to about 20° C.

DESCRIPTION OF THE PREFERRED EMBODIMENTS

An embodiment of the present invention is a process for preparing a compound having the formula $$R-CH_2-\underset{\underset{NH_2}{|}}{\overset{\overset{CH_2F}{|}}{C}}-COOH \qquad (I)$$

wherein R is an aryl group which comprises reacting a compound having the formula $$R-CH_2-\underset{\underset{NH_2}{|}}{\overset{\overset{CH_2OH}{|}}{C}}-COOH \qquad (II)$$

with (a) $SF_4$ and (b) $BF_3$ or $AlCl_3$, in liquid HF at temperatures ranging from about −80° C. to about 20° C.

R is an aryl group exemplified by

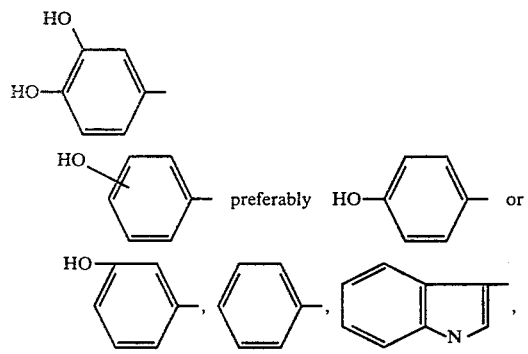

preferably

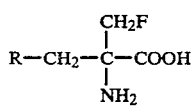

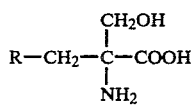

-continued

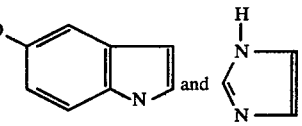 and 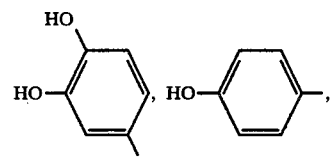

Preferred R groups are

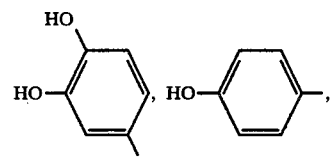

and

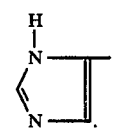.

The compounds of formula I and II have a chiral center and may occur in optically active forms i.e., as optical isomers. These isomers are designated conventionally by the symbols L and D, − and +, l and d, S and R and combinations thereof. Where the compound name or formula has no isomer designation, the name of formula includes the individual isomers, mixtures thereof and racemates.

The present process is preferably carried out at atmospheric pressure although pressures above atmospheric may be used. The reaction temperature ranges from about −80° C. to about 20°, −80° C. to 0° C. being preferred.

The present process may conveniently be carried out by introducing the $SF_4$ and $BF_3$ or $AlCl_3$ into the Formula II/HF reaction system initially. The process may also be carried out by first adding the $SF_4$ to the reaction system, allowing the reaction to proceed for a period of time and then adding the $BF_3$ or $AlCl_3$ and allowing the reaction to go to completion.

The use of $BF_3$ or $AlCl_3$ in the $SF_4$/HF reaction system substantially improves the yield of Formula I product.

The formula I products have decarboxylase inhibiting activity and are useful as diagnostic tools to determine the presence and importance of the corresponding decarboxylase in relation to diseases as to functioning of biological systems. The products may also have chemotherapeutic utility which is a consequence of their decarboxylase inhibiting activity. For example, α-fluoromethylhistidine inhibits the biosynthesis of histamine from histidine and thus may be useful in preventing gastric lesions or in treating allergic conditions.

α-Fluoromethyl-3-hydroxytyrosine and α-fluoromethyl tyrosine also exhibit antihypertensive activity when administered to spontaneously hypertensive (SH) rats; the compounds are thus indicated to be useful for treating hypertension in humans.

The following examples illustrate the process of the present invention. All temperatures are in °Centigrade. Melting points are determined in open capillary and are uncorrected.

EXAMPLE 1

Preparation of S-alpha-Fluoromethyl-3-Hydroxy-Tyrosine

(A) Preparation of R-α-hydroxymethyl-3-hydroxy-tyrosine 50 g of 3-[3',4'-diacetoxyphenyl]-2-acetamino-2-acetoxymethyl-propionic acid is added into 204 ml of 4 M aqueous KOH with stirring. After 1 hour of stirring (under nitrogen), the solution contains potassium salt of 3(3',4'-dihydroxyphenyl)-2-acetamino-2-hydroxymethyl-propionic acid, formed in essentially quantitative yield. Without isolation, by methylation with dimethyl sulfate, this compound is transformed into 3-(3',4'-dimethoxyphenyl)-2-acetamino-2-hydroxymethyl-propionic acid. This operation is performed at room temperature under $N_2$ gas by dropwise addition with vigorous stirring of dimethyl sulfate (about 64 ml) and 4 M aqueous KOH solution (about 148 ml) over a period of about 1 hour.

The reaction mixture was stirred for another hour, then left standing overnight. Acidification (at 5°-10° C. with 55 ml of conc. aqueous HCl), extraction with ethyl acetate (12×300 ml), drying over $Na_2SO_4$ and evaporation in vacuo gave R,S-3(3',4'-dimethoxyphenyl)-2-acetamino-2-hydroxymethyl-proionic acid. It was purified by recrystallization from 1325 ml of acetonitrile, m.p. 154°-6° C. (dec.).

Twenty-nine and 1/10 g of strychnine was suspended in 1.12 l of ethanol 2BA, heated to reflux, then 26.1 g of R,S-3(3',4'-dimethoxyphenyl)-2-acetamino-2-hydroxymehtyl-propionic acid was added. The solution thus obtained was allowed to cool down and left standing overnight at room temperature. Crystals of the strychnine salt of antimer, "A" separate; m.p. 193°-194° C. ("HM").

The mother-liquor of the above named precipitation was evaporated in vacuo to dryness and recrystallized from 270 ml of ethanol 2BA; the hot solution is allowed to cool to room temperature and left standing at room temperature for ~3 hours, then kept in the refrigerator for ~4 hours. The crystals formed were collected on a filter and after drying, recrystallized from acetonitrile to give strychnine salt of antimer "B" of 3-(3'4'-dimethoxyphenyl)-2-acetamino-2-hydroxymethyl-propionic acid m.p. 130°-132° C. (dec.). Yield 17.5 g.

Seventeen g of this strychnine salt was decomposed by dissolving it first in 160 ml of water; 31 ml of 1 M aq. NaOH solution was added. The strychnine separated was removed by filtration and the solution evaporated to small volume in vacuo and applied onto a small ion exchange resin column (150 ml of AG-$X_2$ cation exchange Dowex 50 resin, 200/400 mesh). Elution with water, followed by evaporation in vacuo of the fractions which showed absorption, as indicated by an LKB UV absorption monitor (UVICORD II-8300). This compound, antimer "B" of 3-(3',4'-dimethoxyphenyl)-2-acetamino-2-hydroxymethyl-propionic-acid showed $[\alpha]_D$: 78.3+0.5° (C, 1.425 in 0.1 M aq. NaOH).

Transformation of the above compound into the corresponding stereo-isomer of α-hydroxymethyl-3-hydroxytyrosine: Four and 43/100 g of antimer "B" of 3-(3',4'-dimethoxyphenyl)-2-acetamino-2-hydroxymethylpropionic acid is dissolved in 100 ml conc. HCl and sealed and heated for 90 minutes in a Fisher-Porter tube immersed into an oil bath of 130° C. The solvent was evaporated in vacuo and the above HCl treatment repeated. The residue thus obtained represents R-α-hydroxymethyl-3-hydroxy tyrosine hydrochloride.

(B) FLUORODEHYDROXYLATION 8 g of R-α-hydroxymethyl-3-hydroxytyrosine. HCl is charged to a 1 l. reactor. The reactor is immersed into a dry-ice acetone bath and 80 ml of liquid HF is condensed on top of the substrate. To remove the HCl present, the cooling-bath is removed and the HF solvent removed by passing in a stream of $N_2$ gas. The reactor is immersed into the cooling bath again a stream of HF gas is passed in until a liquid volume of ·250 ml collects. 6.2 ml of $SF_4$ (17.6 mmol/ml: ~109 mmol) is then bubbled in, the solution aged for 1 hour, the cooling bath exchanged for an ethylene-glycol bath kept at −16° C. and the solution aged for ~22 hours. Boron trifluoride gas is passed in until saturation and the solution aged again at −16° C. for 46 hours. The cooling bath is removed and the solvent evaporated by passing through it a vagorous steam of $N_2$ gas. The residue is quenched in ~100 ml of ice-cold aqueous HCl (2.5 M), evaporated in vacuo, the residue dissolved in water and added onto a column of cation-exchange resin. 2.2 l of AG-50-X-8 resin (200/400 mesh) was employed. Elution with 0.25 M aq. HCl, containing 5% methanol; in ~8.5 hours, 7.2 l of this solvent is pumped through the column. This is followed by 7.2 l of 0.4 M aq. HCl with 7.5% methanol in 8.5 hours, then concluding with 0.6 M aq. HCl with 10% methanol. 22 ml fractions are collected, 10 tubes per rack. Tubes in racks No 45–66 contained the desired compound. Evaporation in vacuo gave HCl salt of S isomer of α-fluoromethyl-3-hydroxytyrosine.

For liberation of the free amino acid, 4.826 g of this compound was dissolved in 90 ml of isopropanol, filtered through Celite. 6.2 ml of propylene oxide was added to the filtrate and the suspension kept at room temperature for 3.5 hours, then at ~5° C. for another 2.5 hours. The S α-fluoromethyl-2-hydroxy-tyrosine thus formed was collected by filtration, washed with isopropanol and dried overnight in vacuo at 76°. $[\alpha]_D$: +9.3°±0.5, c, 1.82 in 1:1 mixture of trifluoroacetic acid and water.

EXAMPLE 2

Preparation of R-α-Fluoromethyl-3-Hydroxy-Tyrosine

For preparation of the above named compound the strychnine salt of the antimer of 3(3',4'-dimethoxyphenyl)-2-acetamino-2-hydroxymethyl-propionic acid (Example 1 "HM") was carried through steps analogous to those in Example 1. The final product of the sequential steps was R-α-fluoromethyl-3-hydroxy-tyrosine, with $[\alpha]_D$: −9° (c, 2.5 in a 1:1 mixture of $H_2O$-trifluoroacetic acid).

EXAMPLE 3

R,S-α-Fluoromethyl-Tyrosine

One and 5/100 g (0.005 mol) of R,S-α-hydroxymethyl-tyrosine is charged into a reactor. The reactor is immersed into a dry-ice-acetone bath and ~50 ml of liquid HF is collected by passing in a stream of HF gas. Under continuing cooling, $SF_4$ gas (4 ml, measured in liquid state at −78° C.) is passed in, then $BF_3$ gas until saturation at −78° C. (Stirring with magnetic stirrer). The deep-red solution thus obtained is aged overnight at −78° C.; the cooling bath is removed then, and the solvent evaporated to dryness in vacuo. The residue is dissolved in water and applied to a strong acid cation-exchange resin column, prepared with 100 ml of AG50-X-8 resin (200/400 mesh). The column is first washed with water (1.8 l), followed by 0.5 M aq. HCl. 20 ml fractions of the effluent are collected and the course of the elution is followed by UV monitor of LKB, Model UVICORD II. The fractions corresponding to the main peak in the UV curve are combined and evaporated to dryness in vacuo, to yield hydrochloride salt of R,S-fluoromethyl-tyrosine. 400 mg of this salt is dissolved in 6 ml of water; after a few minutes, crystallization of R,S-fluoromethyl-tyrosine begins. After standing overnight at 5° C., the product is filtered, washed with water, ethanol and diethyl-ether and dried in vacuo at 76° C., to give R,S-α-fluoromethyl tyrosine.

EXAMPLE 4

R,S-α-Fluoromethyl-Histidine (FM HIST)

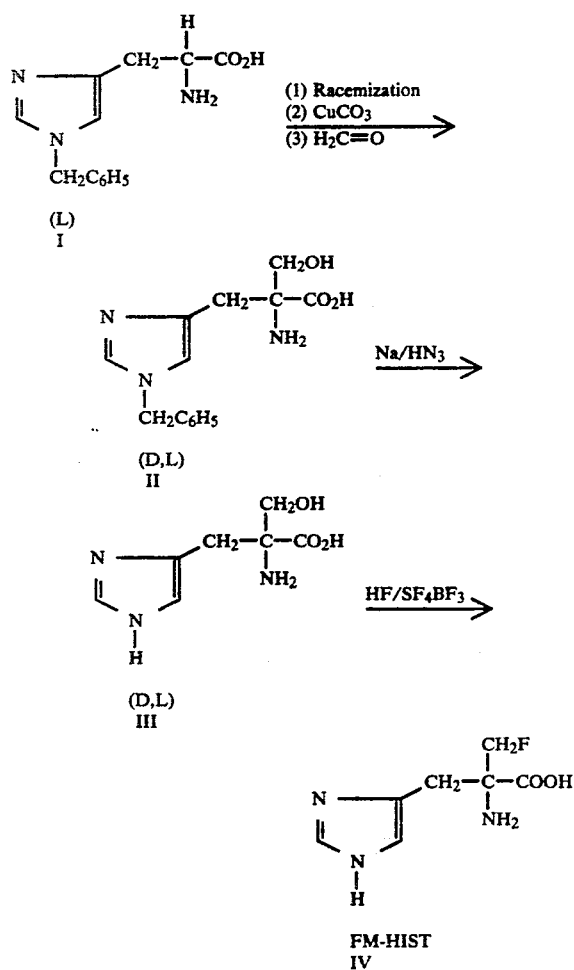

(A) Racemic N(im)Benzyl-Histidine

Thirty g of N(im)Benzyl-L-histidine is dissolved in 600 ml H$_2$O and the solution heated in a high-pressure autoclave at 200° C. for 8 hours with shaking. The autoclave is cooled to room temperature, the clear supernatant solution evaporated in vacuo to dryness to give the R,S-α-fluoromethyl-histidine as a colorless crystal.

(B) R,S-α-Hydroxymethyl-N(im)Benzyl-Histidine (II)

Twenty g of rac. N(im)benzyl-histidine is dissolved in 1 l of hot water, then 40 g of basic cupric carbonate is added in portions and the mixture refluxed with stirring for 1 hour. The mixture is filtered while hot and the filtrate is evaporated in vacuo to give Cu chelate of racemic N(im)benzyl-histidine as a blue solid.

A mixture of 31 ml of formalin (38% H$_2$CO), 3.1 ml of pyridine and 2.13 g of Na$_2$CO$_3$ is heated with stirring to 70° C. then 20 g of the above named Cu-chelate is added and the system heated and stirred at 75° for 90 minutes. Evaporation in vacuo gives a blue solid residue. This is dissolved in a mixture of 50 ml of H$_2$O with 50 ml of conc. NH$_4$OH and charged onto a cation-exchange resin column (Dowex 50-X-8, 300 ml resin in the NH$_4$-form) and eluted with 2 M aq. NH$_4$OH solution. The effluent is monitored with LKB UVICORD II UV absorption monitor and the 1.1 l. portion of the effluent with UV absorption is combined, evaporated in vacuo to a solid. The residue is dissolved in a mixture of 60 ml of H$_2$O with 5 ml of conc. aq. NH$_4$OH and charged onto an anion exchange resin column (300 ml of Dowex 1-X-2 resin in the OH$^-$ form). The column is washed with water (2 l.) and eluted with 2 M aq. HCl, monitored with a UVICORD II for UV absorption. The effluent fractions with ultraviolet absorption were combined and evaporated to dryness, to give substantially pure HCl salt of N(im)benzyl-α-hydroxymethyl-histidine (II) (new compound). This compound is transformed into α-hydroxymethyl-histidine (III) in the following way: 12.5 g of II is dissolved in 200 ml of liquid NH$_3$ (3-neck flask, equipped with "cold-finger" condenser filled with dry-ice-acetone), then sodium is added (5.5 g, cut in small pieces) until the blue color persists for ~10 minutes. NH$_4$Cl is added then to consume the excess the excess Na (indicated by decolorization) and the NH$_3$ solvent is allowed to evaporate under a stream of N$_2$. The product III thus obtained is purified by chromatography on a cation-exchange resin column (2.2 l. of Dowex-50-X-8, 200/400 mesh). Crude III is dissolved in 100 ml of H$_2$O and applied onto the resin column. The column is washed first with water (4 l.) then developed with aq. HCl (1.5 M, then 2 M). 20 ml fractions are collected, flow rate 600 ml/h.

| Fraction No. | | Pauly Reaction |
| --- | --- | --- |
| 1-400 | 1.5M HCl | — |
| 401-670 | 2M HCl | — |
| 671 & later | | + |

Fractions 671-760 are combined and evaporated in vacuo to dryness, to give III: R,S-α-hydroxymethylhistidine 2 HCl (new compound).

(C) R,S-α-Fluoromethyl-Histidine (IV)

Two and 73/100 g of R,S-α-hydroxymethyl-histidine.2 HCl(III) is dissolved in 70 ml of liq. HF, then evaporated to dryness by passing in a stream of N$_2$. The residue thus obtained represents the hydrofluoride salt of α-hydroxymethyl-histidine. It is redissolved in 200 ml of liq. HF (dry-ice-acetone cooling bath), then 9 ml SF$_4$ is passed in (measured as liquid at −78° C.). The solution is stored overnight, while being kept in a cooling bath of −12° C. The solution is saturated then with BF$_3$ gas, left standing for 5 hours, saturated then with BF$_3$ gas, left standing for 5 hours, saturated again at −12° C. and left aging at the same temperature for 66 hours. The cooling-bath is then removed and the solvent evaporated by passing in a stream of N₂. The residue represents mainly HBF₄ salt of α-fluoromethyl-histidine. This is dissolved in 100 ml of 2.5 M aq. HCl, evaporated to dryness and transformed into the HCl salt as follows: It is redissolved in H₂O and applied onto a cation-exchange resin column (100 ml of AG50-X-2, 200/400 mesh), eluted with H₂O until effluent is neutral and free of F⁻. The product is released then from the column by 3 M aq. HCl, evaporated to dryness in vacuo, to result in a residue, consisting mainly of dihydrochloride of IV. For final purification, this is rechromatographed on another AG-50-X-2 column (900 ml resin). Elution with:

0.5 M aq. HCl-1 l.
1.0 M aq. HCl-1.5 l.
1.5 M aq. HCl-3.3 l (collection begins here, 20-ml fractions)
2.0 M aq. HCl-8.00 l.

The desired product IV was located by Pauly test. Fractions 390–470 are combined, evaporated to dryness in vacuo, to give pure dihydrochloride of IV. Recrystallization from water-isopropanol (1:9 v/v) gives the crystalline monohydrochloride salt of α-fluoromethyl-histidine, m.p. 226°–7° (dec.).

EXAMPLE 5

Synthesis of R,S-α-Fluoromethyl-Ornithine (A) R,S-α-Hydroxymethyl-δ-N-Benzoyl-Ornithine Copper chelate of R,S-δ-N-benzoyl-ornithine (7.995 g) is added in small portions onto a mixture made of formalin (38% H₂CO; 12.45 ml), pyridine (1.25 ml), and sodium carbonate (0.81 g) at ∼70° C., under mechanical stirring. After further 90 minutes stirring at 75° C., it is evaporated to dryness in vacuo, the dark blue residue dissolved in a mixture of 30 ml of H₂O and 30 ml of conc. aq. NH₃ solution and charged to a cation-exchange resin column (130 ml of Dowex 50-X-8 in the NH₄⁺ form) to remove Cu²⁺. The column is eluted with 250 ml of 2 M aq. NH₃ and the effluent evaporated to dryness in vacuo. The residue is redissolved in H₂O and applied onto an anion exchange resin column (Dowex 1-X-2, OH⁻ form, 130 ml resin). The column is washed with H₂O (250 ml) and eluted with 3 M aq. HCl. The HCl effluent is concentrated in vacuo to give R,S-α-Hydroxymethyl-δ-N-Benzoyl-Ornithine.

(B) R,S-α-Hydroxymethyl-Ornithine Dihydrochloride

Three and 5/10 g of the product obtained in (a) is dissolved in 40 ml of 6 M aq. HCl and refluxed for 21 hours. The solution is extracted with toluene (2×40 ml) and the aqueous phase evaporated in vacuo to dryness, to give R,S-α-hydroxymethyl-ornithing dihydrochloride (new compound).

(C) R,S-α-Fluoromethyl Ornithine

One and 1/10 g of the product obtained under (b) is placed into a reactor, the reactor immersed into a dry-ice-acetone bath and HF gas passed in until HF solution of ∼25 ml volume is formed in the reactor. The cooling bath is removed and the solvent evaporated by passing in a stream of N₂. The residue thus obtained represents the HF salt of R,S-α-hydroxymethyl-ornithine. This residue is redissolved in HF, by cooling the reactor in the dry-ice-acetone bath and passing in HF gas until 50 ml volume is reached. SF₄ gas is passed in (4 ml as measured in liquid state at −78° C.), the dry-ice-acetone cooling bath removed and replaced by a bath kept at −15° C. After aging for 16 hours at −15° C., BF₃ gas is passed in for saturation. After 5 hours further aging, the cooling bath is removed and the solvent evaporated by passing in a stream of N₂. The residue is dissolved in 6 M aq. HCl, evaporated to dryness in vacuo and redissolved in H₂O (10 ml). This solution is applied onto a Dowex 50-X-8 cation-exchange resin column (400 ml resin, 200/400 mesh, H⁺ form). The column is first washed with H₂O (800 ml); elution with 2 M aq. HCl, 15 ml fractions are collected. Flow rate 600 ml/h. Every 5th fraction is spotted on TLC plate and developed with ninhydrin spray. Fractions No. 171–220 are combined and evaporated to dryness in vacuo, to deliver a mixture of amino acids, the main component being R,S-α-fluoromethyl-ornithine.2 HCl. For further purification, this product is rechromatographed on another column, made of Dowex 50-X-8 cation exchange resin (200/400 mesh). For development, the dolumn is first washed with water, then eluted with 1.5 aq. HCl, flow rate 0.6 l./h. 20-ml fractions are collected. The residue obtained on evaporation of fractions No. 521–540 represents pure R,S-α-fluoromethyl-ornithine dihydrochloride.

Claims to the invention follow.

We claim:

1. In a process for preparing compounds having the formula

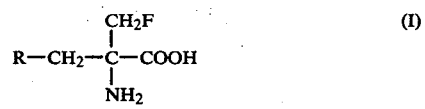

wherein R is

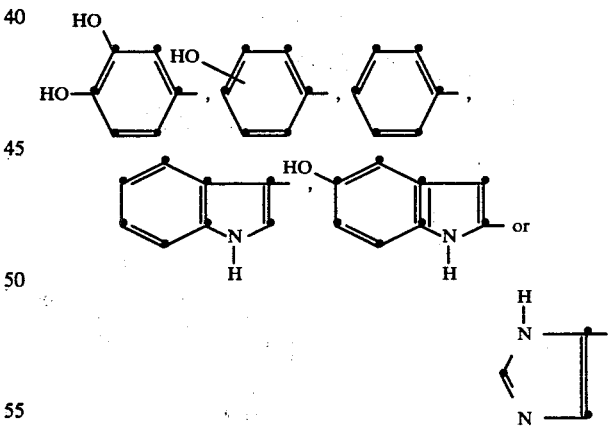

by reacting a compound having the formula

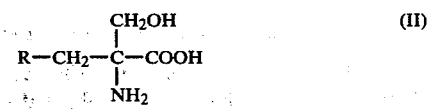

with SF₄ in liquid HF at temperatures ranging from about −80° C. to about 20° C., the improvement which comprises adding AlCl₃ to the reaction system.

2. The process of claim 1 wherein R is

3. The process of claim 1 wherein said temperature is −80° C. to about 0° C.
4. The process of claim 3 wherein R is
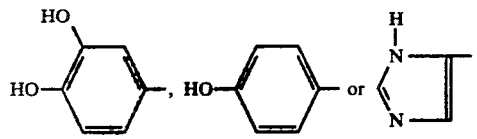
5. The process of claim 3 wherein R is
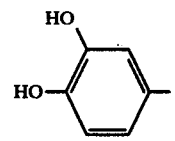
6. The process of claim 3 wherein R is
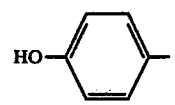
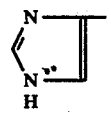
* * * * *